(12) United States Patent
Sklar et al.

(10) Patent No.: US 6,547,778 B1
(45) Date of Patent: Apr. 15, 2003

(54) GRAFT LIGAMENT STRAND TENSIONER

(76) Inventors: Joseph H. Sklar, 210 Park Dr., Longmeadow, MA (US) 01106; Greta Jo Hays, 1702 E. 1030 North, Logan, UT (US) 84341; T. Wade Fallin, 210 E., 200 South, Hyde Park, UT (US) 84318; Daniel F. Justin, 185 N. Winding Way, Logan, UT (US) 84321

( * ) Notice: Subject to any disclaimer, the term of this patent is extended or adjusted under 35 U.S.C. 154(b) by 0 days.

(21) Appl. No.: 09/620,927

(22) Filed: Jul. 21, 2000

(51) Int. Cl.[7] ............................................... A61B 17/00
(52) U.S. Cl. ........................................ 606/1; 623/13.13
(58) Field of Search ............................ 606/1, 148, 139, 606/144, 102; 623/13.13, 2.11, 13 FOR

(56) References Cited

U.S. PATENT DOCUMENTS

| | | | |
|---|---|---|---|
| 5,980,473 A | * 11/1999 | Korakianitis et al. | ....... 606/148 |
| 6,019,790 A | * 2/2000 | Holmberg et al. | ......... 623/2.11 |
| 6,074,418 A | * 6/2000 | Buchanan et al. | ......... 623/2.11 |
| 6,171,310 B1 | * 1/2001 | Giordano et al. | ............. 606/60 |

* cited by examiner

Primary Examiner—Bruce Snow
Assistant Examiner—Brian E Pellegrino
(74) Attorney, Agent, or Firm—Pandiscio & Pandiscio

(57) ABSTRACT

A graft ligament strand tensioner includes a frame member for slidingly retaining loops of sutures extending from graft ligament strands. The tensioner further includes a collar portion, and is provided with a handle having a core portion on which the collar portion is disposed for axial movement, and a grip portion. The tensioner still further includes a spherical member connected to the handle and having rounded surfaces facing the collar portion. The collar portion is tiltingly movable on the spherical member rounded surfaces when manipulation of the handle, to pull sutures on the frame member taut, causes the collar portion to engage the spherical member rounded surfaces. The sliding retention of the sutures and the tilting movement of the collar portion provide substantial equalization of tension in the sutures and thereby the graft ligament strands.

16 Claims, 5 Drawing Sheets

GRAFT LIGAMENT STRAND TENSIONER

FIELD OF THE INVENTION

This invention relates to medical devices in general, and more particularly to a device for positioning and tensioning a plurality of graft ligament strands simultaneously, equally, and to a selected tension.

BACKGROUND OF THE INVENTION

It is known to use four combined strands, such as two (doubled) gracilis strands and two (doubled) semitendinosus strands, in reconstruction of the anterior cruciate ligament (ACL). It is further known to use other numbers of strands, such as one, two or three. It is also known to use other grafts, such as patellar tendon, quadriceps tendon, tibialis, and the like. When using more than one strand, it is preferred that the pluralities of ligament strands be equally tensioned, inasmuch as the strands must be under equal tension in order to provide optimum biomechanical properties. The tension on each ligament may be applied by hand one ligament at a time, but it has been demonstrated that applying tension by hand is not effective in equalizing the load on the various tendon strands. An improvement has been realized by tensioning the strands with applied weights as, for example, by hanging a weight from each tendon strand. While the use of such weights provides a known tension and equalization of tensions, the handling of the weights in the course of an ACL reconstruction has proven awkward and laborious.

Accordingly, there is a need for a device by which a plurality of graft ligament strands may be tensioned simultaneously, equally, to a desired tension, and positioned to a desired orientation.

OBJECTS OF THE INVENTION

An object of the invention is to provide a graft ligament strand tensioner having facility for tensioning one or a plurality of graft ligament strands simultaneously, equally, and to a selected tension, and to a desired position.

Another object of the invention is to provide an improved method for reconstructing a ligament.

SUMMARY OF THE INVENTION

With the above and other objects in view, as will hereinafter appear, a feature of the invention is the provision and use of a graft ligament strand tensioner comprising a frame member for slidingly retaining loops of suture strands attached to and extending from the ligament strands and having a collar portion, a cylinder having a spherical portion and on which the collar portion is mounted for pivoting movement, a grip portion for manipulation by an operator to apply tension to the strands, a stop member connected to the cylinder, and a spring disposed within a space between the grip portion and the cylinder, the spring being retained by the stop member. The collar portion is tiltingly movable on the cylinder member spherical portion surfaces when manipulation of the grip portion, to pull strands on the frame member taut, causes the stop member to compress the spring portion. The sliding retention of the strands and the pivoting movement of the collar portion provide substantial equalization of tension in the strands.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

The above and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE INVENTION

Figure 1:
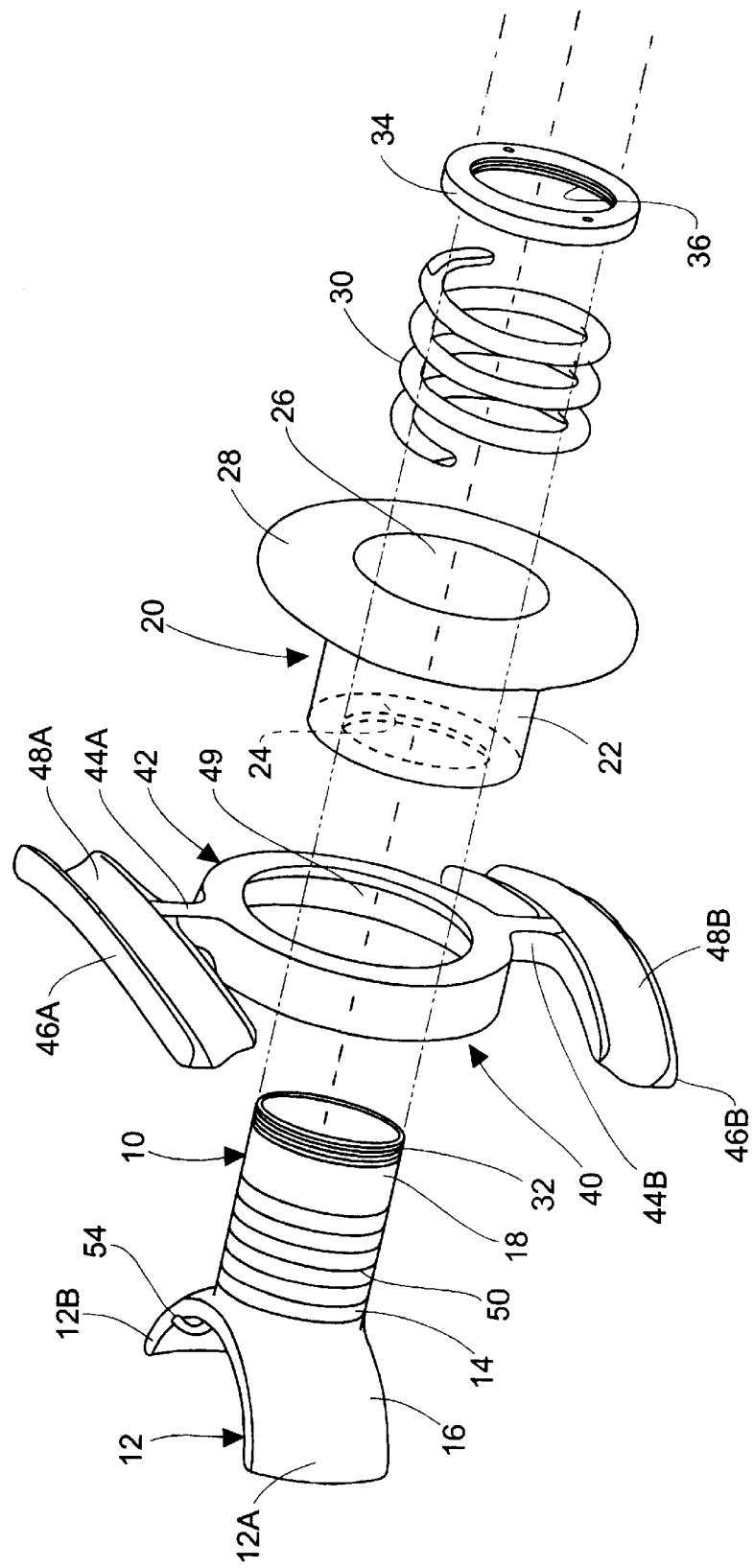
FIG. 1 is an exploded perspective view of one form of ligament strand tensioner illustrative of an embodiment of the invention.
Figure 2:
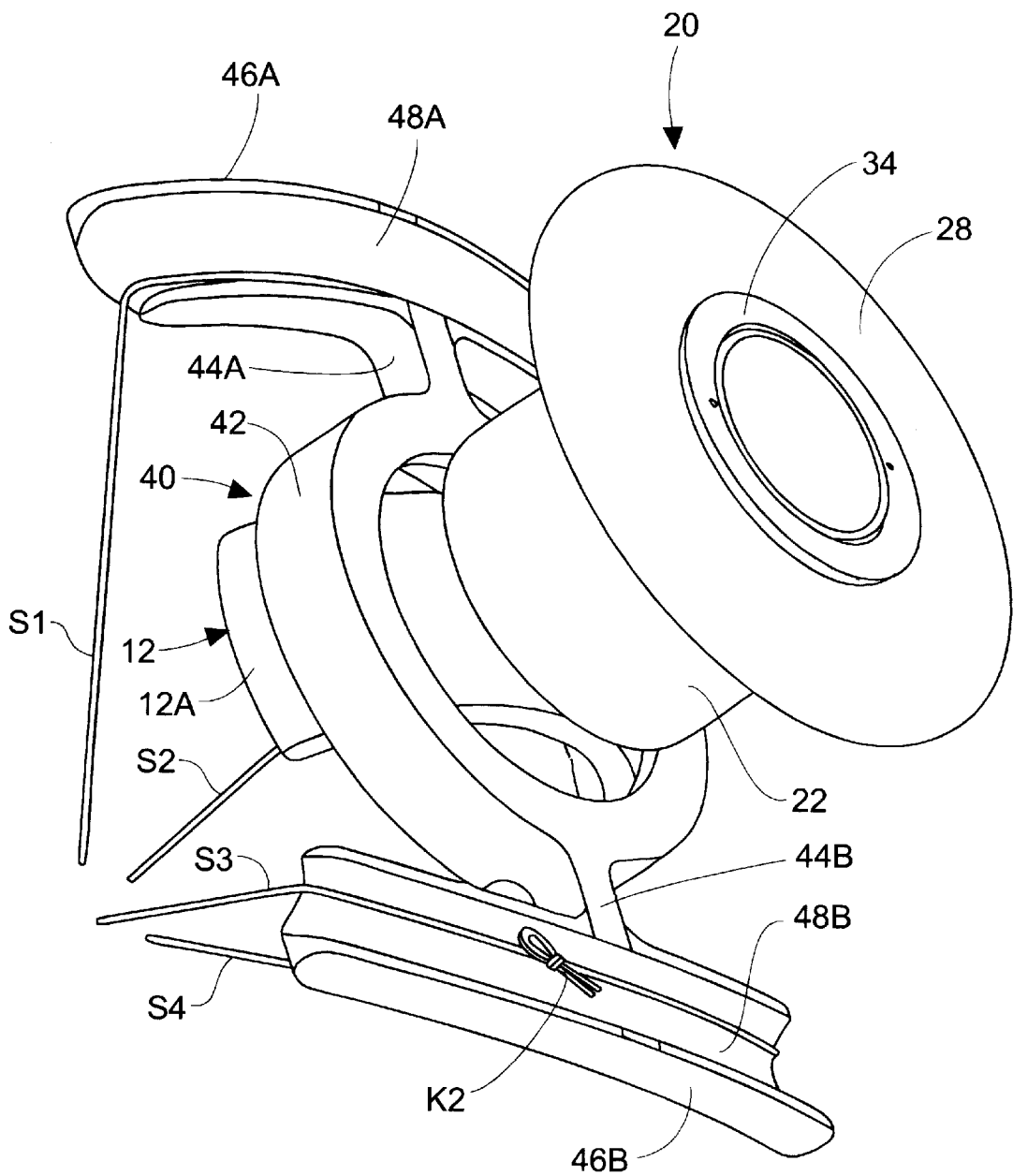
FIG. 2 is a perspective view of the parts of FIG. 1 assembled and having sutures mounted thereon.
Figure 3:
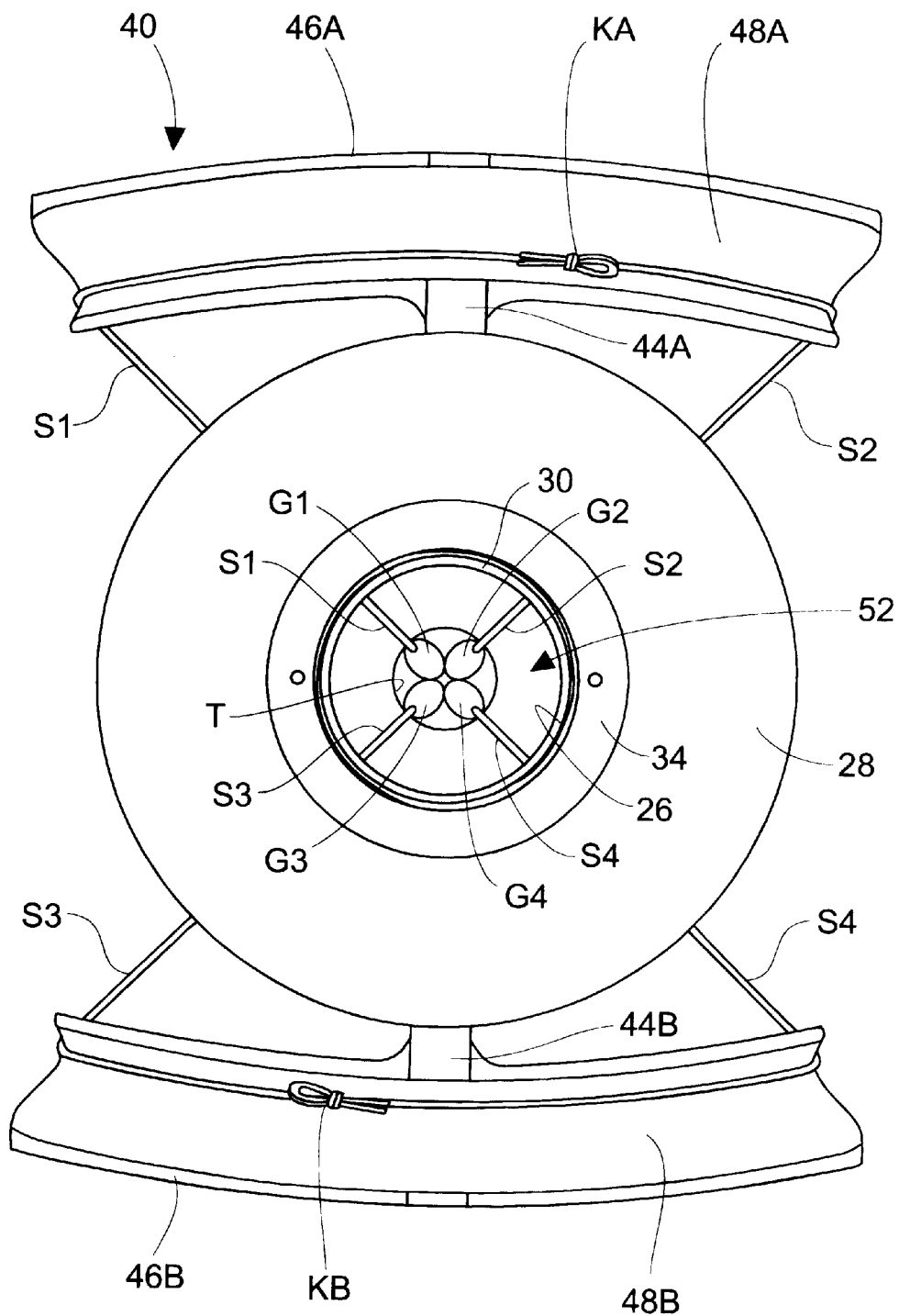
FIG. 3 is a front elevational view of the assembly of FIG. 2.

Referring first to FIG. 1, it will be seen that the illustrative graft ligament strand tensioner includes a rigid cylindrically-shaped tube 10 and, extending outwardly therefrom, a spherically curved section 12. Spherically curved section 12 extends from a distal end 14 of tube 10 and comprises a curved member with portions 12A and 12B extending outwardly on either side, respectively, of tube 10. Each of the portions 12A and 12B is provided with a rounded, preferably spherically-shaped, proximally-facing surface 16.

Alternatively, instead of the spherically curved section 12 there may be provided other universal-joint type connections or abutment members (not shown) affording pivoting abutment with another member.

Figure 5:
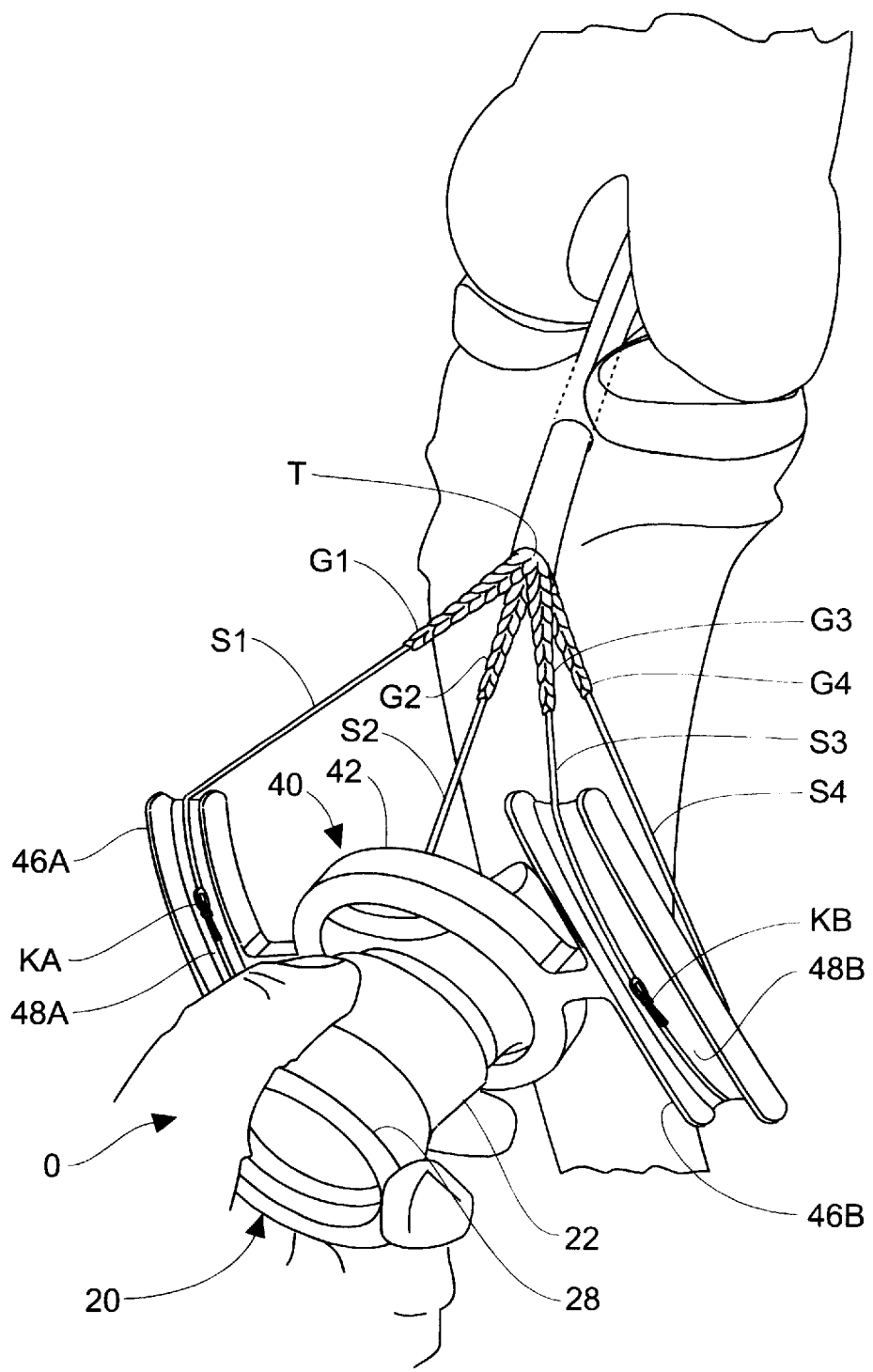
FIG. 5 is a perspective view of the tensioner in use.
Figure 1:
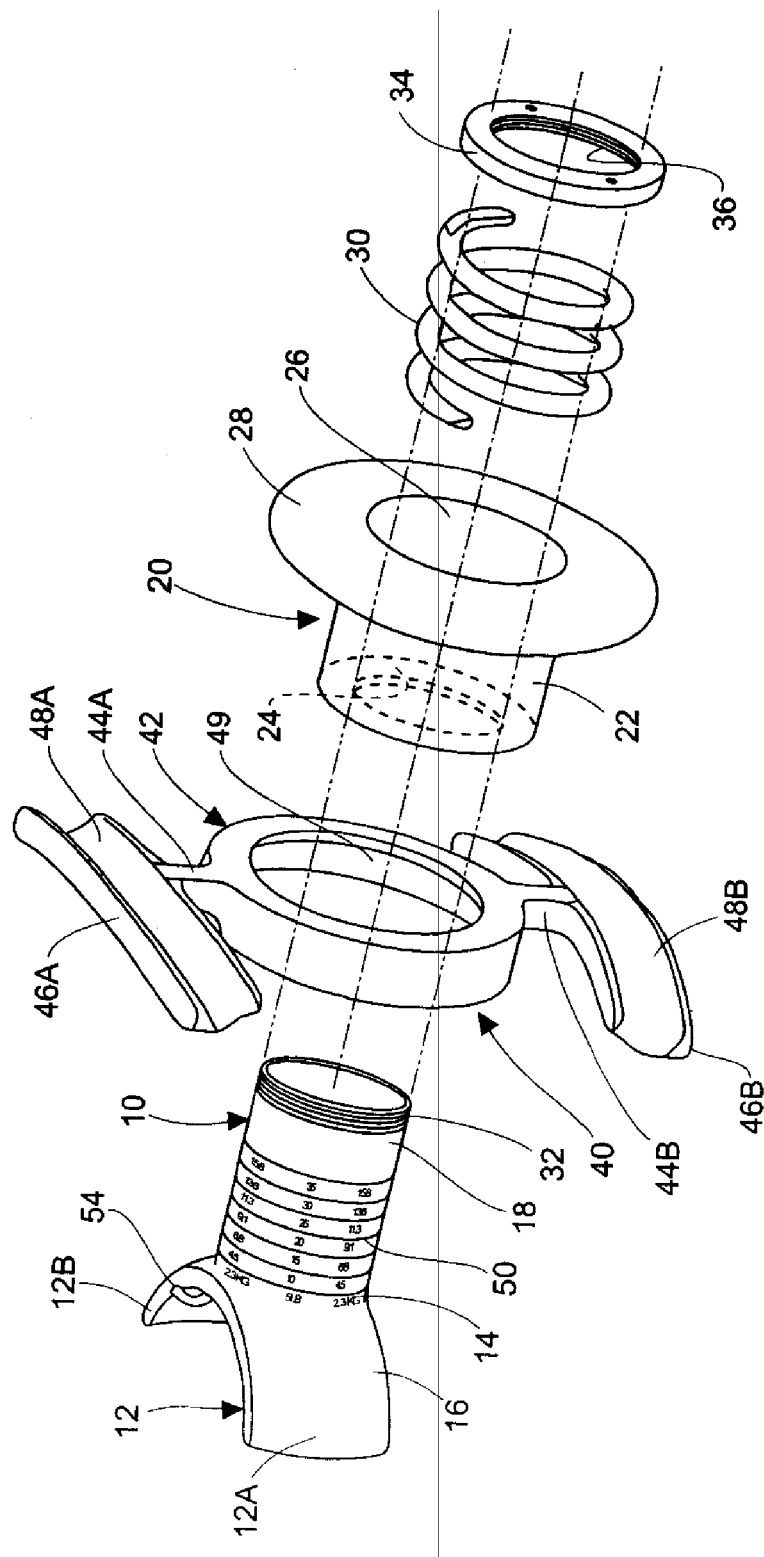
Figure 4:
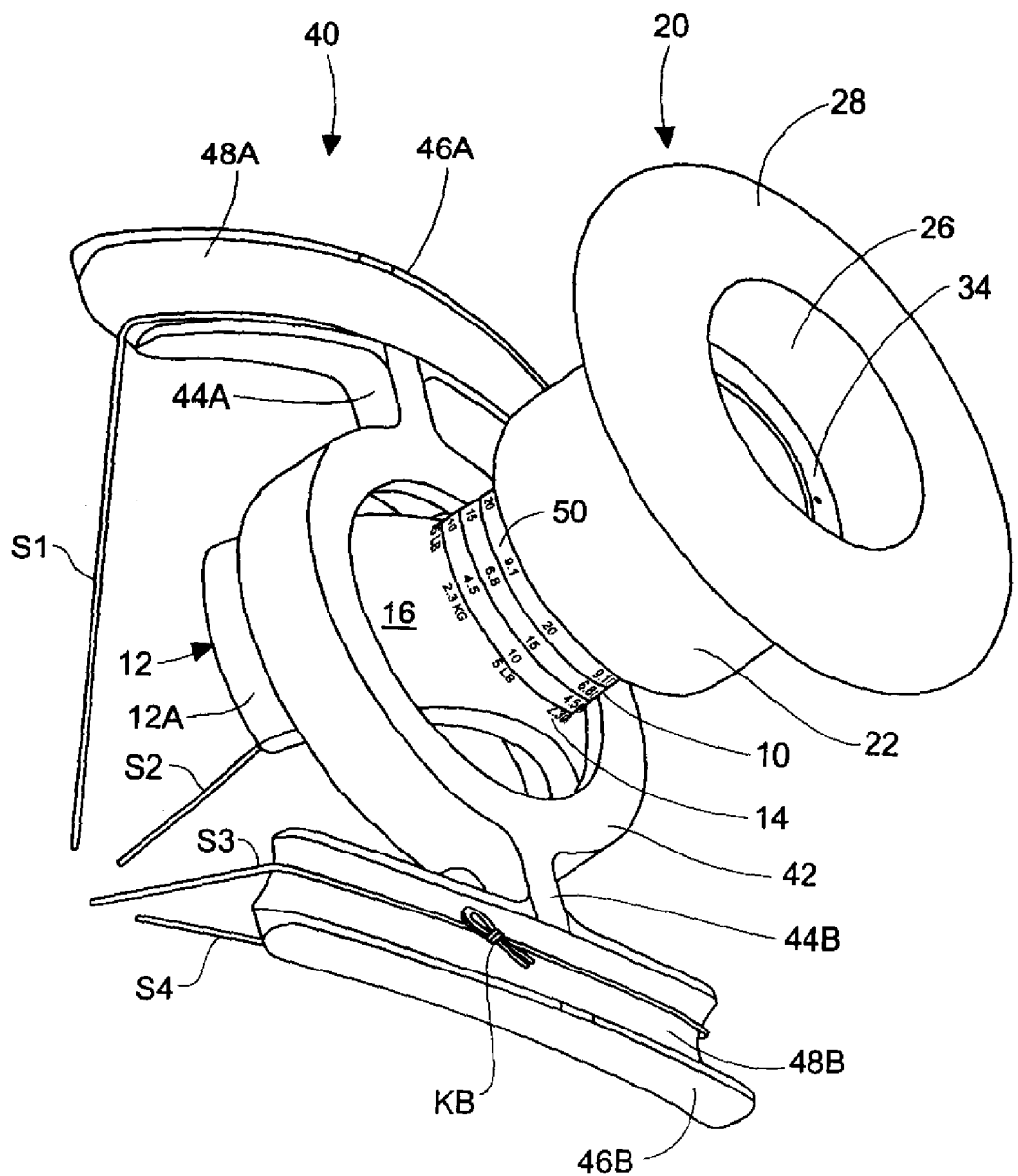

The tensioner further includes a handle 20 having a tubular core portion 22 mounted on tube 10. Handle 20 is further provided with a grip portion 28 by which an operator 0 (FIG. 5) may grasp and operate the device. Grip portion 28 may be in the form of an annularly-shaped flange portion extending outwardly from a proximal end of core portion 22. The grip portion shown herein is circular in configuration, but alternative handles (not shown) include flanges, U-shaped handles, pistol grips, and the like. The handle should be adapted for single handed use and provide an adequate grip surface. Core portion 22 is provided with an internal ledge 24 through which tube 10 extends.

A coil spring 30 is mounted between the outer wall of the tube 10 and the inner wall of handle core portion 22. A proximal end 18 of tube 10 is provided with external threads 32. A stop member, in the form of an annular ring 34, is provided with internal threads 36, is disposed in a central opening 26 of handle 20, and is threadedly fixed on proximal end 18 of tube 10. Spring 30 extends between handle ledge 24 and ring 34.

The tensioner further includes a frame member 40 having a collar portion 42 mounted on spherical member 12. Collar portion 42 is provided with a spherical-configured internal surface 49 which is complementary with and engageable with spherical member spherical surfaces 16 and movable thereupon in a pivoting or tilting fashion. Alternatively, as noted above, instead of the spherically curved section 12, there may be provided other universal-joint type connections or abutment members (not shown) affording pivoting abutment with another member. The frame member 40 is further movable axially along the core portion 22 as a result of motion of tube 10, as described hereinbelow. Opposed struts 44A, 44B extend in opposite directions outwardly from collar portion 42. Fixed on the outward end of each strut 44A, 44B is a rail 46A, 46B having a groove 48A, 48B therein.

Figure 4:
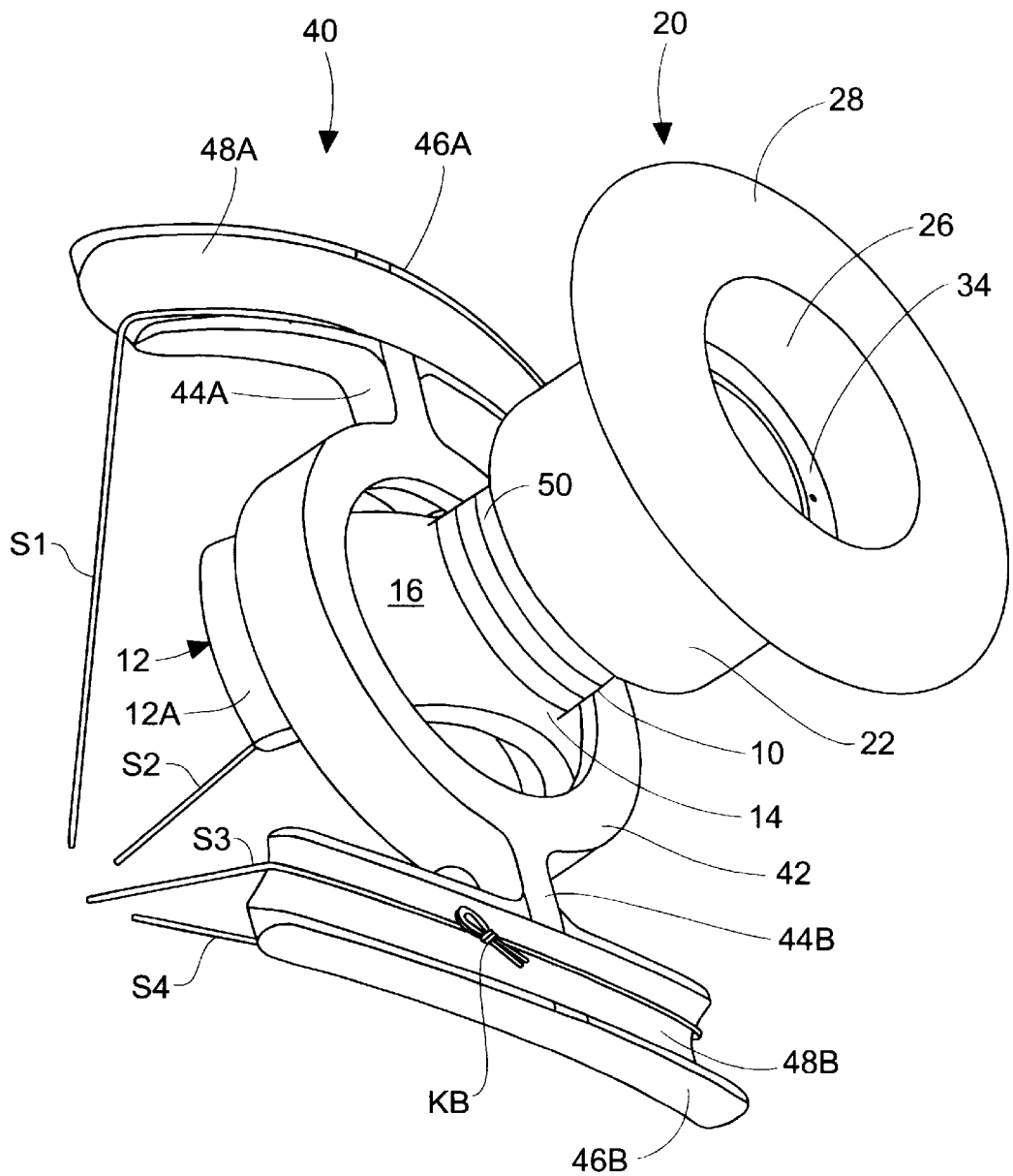
FIG. 4 is similar to FIG. 2, but illustrative of the assembly in a different operational position.

As shown in FIGS. 1 and 4, tube 10 is provided with indicia 50 by which the degree of tension exerted on the ligament strands may be observed during the course of operation of the device, as will be discussed further hereinbelow.

In operation, particularly with respect to the aforementioned ACL replacement procedure, at about five inches from the tibial tunnel opening T (FIG. 5), sutures S1 and S2, extending from gracilis graft ligament strands G1 and G2, are tied together, as at knot KA (FIGS. 2–5) and looped around rail 46A and placed in groove 48A. Similarly, sutures S3 and S4, extending from semitendinosus graft ligament strands G3 and G4, are tied together, as at knot KB and looped around rail 46B and placed in groove 48B.

The operator O, holding the device by handle grip portion 28, pulls the device proximally (FIG. 5), causing ledge portion 24 of handle 20 to compress spring 30, applying a load to ring 34 and tube 10. The load is transmitted to frame 40 through the spherical mating surfaces 12A, 12B and 49. As the load is transmitted from the frame to the sutures, S1, S2, S3, S4, the frame may pivot at the spherical surfaces and the sutures may slide in the rail grooves 48A, 48B so as to equalize tension on the ligament strands G1, G2, G3 and G4.

As handle 20 is pulled proximally by the operator O, and frame member 40 is restrained from further proximal movement by the sutures S1, S2, S3 and S4, handle 20 moves against the bias of spring 30 to expose indicia 50 on tube 10, as shown in FIG. 4. At the same time, collar portion 42 tilts upon spherically curved section 12 to equalize tension in the ligament strands, as aforesaid. Indicia 50 on tube 10 may be in pounds, and/or kilograms, of force, or in any selected units of force, such that the operator may determine, during the tensioning operation, when a selected degree of tensioning has been reached.

The tendons are held in the desired position, with the desired separation, due to the applied force and strut configuration.

The graft tendon strands G1, G2, G3 and G4 are then fixed in the tibial tunnel opening T by a selected one of several known fixation techniques, e.g., by an interference screw or by the Intrafix™ device made by Mitek Surgical Products of Westwood, Mass. Such fixation occurs with all the tendon strands having equal tension thereon and with the tension at a selected tension.

After completion of fixation, the exposed tendons and sutures are snipped off at the tunnel opening T, or secured with additional fixation devices if desired.

In the course of the tension setting operation, if it is desirable to observe and/or treat the area of the tunnel opening T, the device provides a central opening 52 therethrough (FIG. 3), facilitating visualization of the site and the application of instruments thereto, collinearly through the tensioner device. The central opening 52 is substantially collinear with the axis of the bone tunnel T. However, the opening 52 is sufficiently large to accommodate surgical instruments and implants needed, and to permit a degree of eccentricity between the axis of the opening 52 and the axis of the bone tunnel opening T, while still permitting the use of the instruments and implants collinearly with the bone tunnel.

There is thus provided a graft ligament strand tensioner having facility for tensioning up to four graft ligament strands simultaneously and equally, and to a selected degree of tension. It will be apparent that two strands can be tensioned by looping each suture strand over a rail.

Accordingly, equal tension in a plurality of graft strands is effected by permitting differential displacement of each graft strand in its respective groove as tension is applied. The device automatically adjusts for the differential displacement of two or more strands, in the grooves, allowing the suture to move freely to equilibrate tension in the ligament strands attached thereto. It will be apparent that the suture receiving means in the device may be other than the grooves shown herein, as, for example, pulleys, hooks, protrusions, and the like, (not shown). The suture receiving means must, however, be capable of receiving the suture knots KA, KB and allow the knots to pass freely therein. In operation, the ligament strands are retained in a desired orientation relative to the bone tunnel, When four strands are manipulated, for example, the rails hold the sutures at 90° intervals, which facilitates installation of a fixation device in the center of the tunnel. The device is operated without points of contact on the patient; no anchoring straps, holes, or the like, are required.

Referring to FIG. 1, it will be seen that there is a provision for tensioning one strand, by looping a suture over a suture hook 54. This bypasses the frame because the frame is not needed to equalize tension in one strand. However, the device permits selectively tensioning one strand, using the aforementioned indicia 50.

There is further provided an improved method for reconstructing a ligament.

It is to be understood that the present invention is by no means limited to the particular construction and method steps herein disclosed and/or shown in the drawings, but also comprises any modification or equivalent within the scope of the claims.

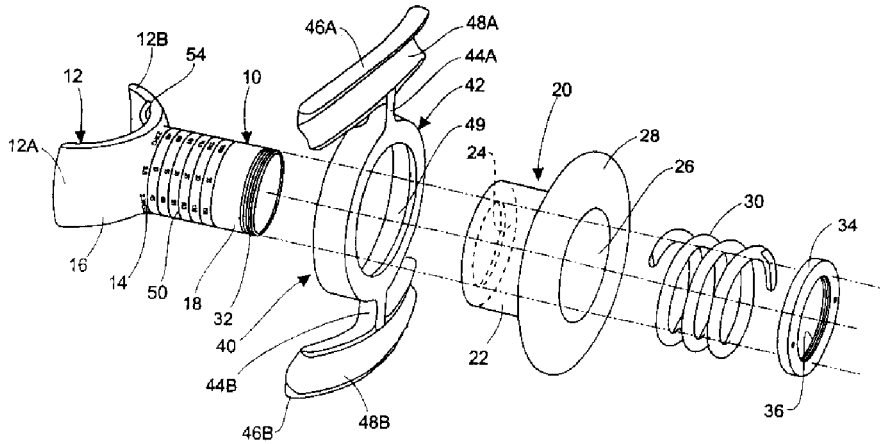

What is claimed is:

1. A ligament strand tensioner comprising:
   a frame member for slidingly retaining loops of suture strands extending from ligament strands, and having a collar portion;
   a cylincdrically-shaped tube on which the collar portion is mounted;
   a spherically curved section fixed at a distal end of said tube; and
   a handle connected to said tube;
   the collar portion being tiltingly movable on said spherically curved section when manipulation of said handle, to pull the suture strands on said frame member taut, causes said spherically curved section to engage the collar portion;
   wherein proximal axial movement of said frame member effects application of the tension on the strands;
   wherein the sliding retention of the suture strands and the tilting movement of the collar portion provide substantial equalization of tension in the ligament strands; and
   wherein said tensioner further comprises a spring, biasing said handle against proximal movement of said handle, on the tube.

2. A ligament strand tensioner in accordance with claim 1 wherein the handle core portion is provided with an inwardly-extending ledge, the spherical tube is provided with a stop member on a proximal end thereof, and said spring comprises a coil spring extending from the ledge to the stop member.

3. A ligament strand tensioner in accordance with claim 2 wherein the tube proximal end is provided with external threads and the stop member is provided with internal threads, and the stop member is threadedly connected to the tube proximal end.

4. A ligament strand tensioner comprising:
 a frame member for slidingly retaining loops of suture strands extending from ligament strands, and having a collar portion;
 a cylindrically-shaped tube on which the collar portion is mounted;
 a spherically curved section fixed at a distal end of said tube; and
 a handle connected to said tube;
 the collar portion being tiltingly movable on said spherically curved section when manipulation of said handle, to pull the suture strands on said frame member taut, causes said spherically curved section to engage the collar portion;
 wherein proximal axial movement of said frame member effects application of the tension on the strands;
 wherein the sliding retention of the suture strands and the tilting movement of the collar portion provide substantial equalization of tension in the ligament strands; and
 wherein said frame member is provided with first and second rails fixed to the collar portion, each of the rails having a groove therein for the sliding retention of one of the loops of suture strands.

5. A ligament strand tensioner comprising:
 a cylindrically-shaped tube;
 a base member extending from the tube and having a spherically curved section at a distal end of said tube;
 a handle having a tubular core portion and a grip portion, said core portion being mounted on said tube and having an internal protrusion;
 a stop member fixed to a proximal end of said tube;
 a spring mounted in said core portion and extending from said internal protrusion to said stop member; and
 a frame member disposed on said core portion and having suture strand rails thereon for retaining suture strands extending from ligament graft strands, said tube being movable axially relative to said frame member whereby said frame member may be engaged by said base member, with said frame member being tiltingly movable along said spherically curved section, to provide equalization of tension in the suture strands retained on the rails, and thereby in the ligament strands.

6. A ligament strand tensioner in accordance with claim 5 wherein said base member comprises opposed first and second outwardly-extending stop portions, each of said stop portions having curved surfaces thereon.

7. A ligament strand tensioner in accordance with claim 6 wherein said frame member comprises a collar portion movably disposed on the handle core portion, the rails being fixed to said collar portion.

8. A ligament strand tensioner in accordance with claim 7 wherein said collar portion is provided with rounded internal surfaces complementary to said curved surfaces of said spherically curved section.

9. A ligament strand tensioner in accordance with claim 5 wherein said handle core portion is movable axially along the tube portion against a bias of said spring.

10. A ligament strand tensioner in accordance with claim 9 wherein the tube is provided with indicia progressively revealed by the movement of the handle core portion, relative to the tube, against the bias of said spring.

11. A ligament graft strand tensioner comprising:
 a cylindrically-shaped tube;
 a base member extending from a distal end of the tube and having proximally-facing surfaces of spherically curved sectional configuration;
 a handle having a tubular core portion and an annularly-shaped flange portion extending outwardly from a proximal end of the core portion, the core portion being mounted on the tube and having an internal ledge;
 a spring mounted in the core portion and abutting the ledge at a distal end of said spring;
 a stop member fixed to a proximal end of the tube, an proximal end of said spring abutting said stop member; and
 a collar disposed on the handle core portion between the handle flange and the base member, said collar having grooved rails fixed thereto and adapted to retain sutures extending from strands of ligament grafts, said tube being movable axially relative to said collar, whereby said collar may be engaged by said base member, with said collar being movable tiltingly along said surfaces of said spherically curved sectional configuration, to provide equalization of tension in ligament graft strands attached to the sutures retained on the grooved rails.

12. A ligament strand tensioner in accordance with claim 11 wherein said collar is provided with spherical internal surfaces for the tilting movement of said collar on said surfaces of said spherically curved sectional configuration of the base member.

13. A ligament strand tensioner in accordance with claim 11 wherein the handle tubular core portion is movable axially along the tube against a bias exerted by said spring.

14. A ligament strand tensioner in accordance with claim 13 wherein the tube is provided with indicia thereon, and axial movement of the handle tubular core portion along the tube, against the bias of said spring, serves to progressively reveal portions of the indicia.

15. A ligament strand tensioner in accordance with claim 14 wherein said spring is a coil spring and the indicia progressively revealed are correlated with compression of said spring.

16. A ligament strand tensioner comprising:
 a frame member for slidingly retaining loops of suture strands extending from ligament strands, and having a collar portion;
 a cylindrically-shaped tube on which the collar portion is mounted;
 a spherically curved section fixed at a distal end of said tube; and
 a handle connected to said tube;

the collar portion being tiltingly movable on said spherically curved section when manipulation of said handle, to pull the suture strands on said frame member taut, causes said spherically curved section to engage the collar portion;

wherein proximal axial movement of said frame member effects application of the tension on the strands;

wherein the sliding retention of the suture strands and the tilting movement of the collar portion provide substantial equalization of tension in the ligament strands;

wherein said ligament strand tensioner further comprises an opening for passing instruments through the ligament strand tensioner to engage the ligament strands; and wherein a central axis of the opening is adapted to be off-set from a central opening of a bone tunnel in which the ligament strands are disposed, and wherein the opening is sufficiently large to permit passage of the instruments colinearly from the opening and into the bone tunnel opening.

* * * * *

UNITED STATES PATENT AND TRADEMARK OFFICE
CERTIFICATE OF CORRECTION

PATENT NO. : 6,547,778 B1
DATED : April 15, 2003
INVENTOR(S) : Sklar et al.

It is certified that error appears in the above-identified patent and that said Letters Patent is hereby corrected as shown below:

Title page should be deleted and replaced with the title page on the attached page.

Drawing sheets, consisting of Fig. 1 and 4, should be deleted and replaced with the drawing sheets, consisting of Fig. 1 and 4, as shown on the attached pages.

Signed and Sealed this

Third Day of May, 2005

JON W. DUDAS
*Director of the United States Patent and Trademark Office*

United States Patent
Sklar et al.

(10) Patent No.: US 6,547,778 B1
(45) Date of Patent: Apr. 15, 2003

(54) GRAFT LIGAMENT STRAND TENSIONER

(76) Inventors: Joseph H. Sklar, 210 Park Dr., Longmeadow, MA (US) 01106; Greta Jo Hays, 1702 E. 1030 North, Logan, UT (US) 84341; T. Wade Fallin, 210 E., 200 South, Hyde Park, UT (US) 84318; Daniel F. Justin, 185 N. Winding Way, Logan, UT (US) 84321

( * ) Notice: Subject to any disclaimer, the term of this patent is extended or adjusted under 35 U.S.C. 154(b) by 0 days.

(21) Appl. No.: 09/620,927

(22) Filed: Jul. 21, 2000

(51) Int. Cl.[7] ............................................. A61B 17/00
(52) U.S. Cl. ............................................. 606/1; 623/13.13
(58) Field of Search .......................... 606/1, 148, 139, 606/144, 102; 623/13.13, 2.11, 13 FOR

(56) References Cited

U.S. PATENT DOCUMENTS

| | | | | |
|---|---|---|---|---|
| 5,980,473 A | * | 11/1999 | Korakianitis et al. | 606/148 |
| 6,019,790 A | * | 2/2000 | Holmberg et al. | 623/2.11 |
| 6,074,418 A | * | 6/2000 | Buchanan et al. | 623/2.11 |
| 6,171,310 B1 | * | 1/2001 | Giordano et al. | 606/60 |

* cited by examiner

Primary Examiner—Bruce Snow
Assistant Examiner—Brian E Pellegrino
(74) Attorney, Agent, or Firm—Pandiscio & Pandiscio

(57) ABSTRACT

A graft ligament strand tensioner includes a frame member for slidingly retaining loops of sutures extending from graft ligament strands. The tensioner further includes a collar portion, and is provided with a handle having a core portion on which the collar portion is disposed for axial movement, and a grip portion. The tensioner still further includes a spherical member connected to the handle and having rounded surfaces facing the collar portion. The collar portion is tiltingly movable on the spherical member rounded surfaces when manipulation of the handle, to pull sutures on the frame member taut, causes the collar portion to engage the spherical member rounded surfaces. The sliding retention of the sutures and the tilting movement of the collar portion provide substantial equalization of tension in the sutures and thereby the graft ligament strands.

16 Claims, 5 Drawing Sheets